United States Patent
Da Silva Ferreira et al.

(10) Patent No.: US 9,868,935 B2
(45) Date of Patent: Jan. 16, 2018

(54) COMPOSITION AND METHOD OF STEM CELLS FOR PRESERVATION OF CARDIAC TISSUE

(71) Applicant: CRIOESTAMINAL, SAÚDE E TECNOLOGIA, SA., Cantanhede (PT)

(72) Inventors: Lino Da Silva Ferreira, Coimbra (PT); Isabel Maria Fidalgo Dos Santos Silva Carvalho, Braga (PT)

(73) Assignee: CRIOESTAMINAL, SAÚDE E TECNOLOGIA, SA., Cantanhede (PT)

( * ) Notice: Subject to any disclaimer, the term of this patent is extended or adjusted under 35 U.S.C. 154(b) by 347 days.

(21) Appl. No.: 14/397,122

(22) PCT Filed: Apr. 24, 2013

(86) PCT No.: PCT/IB2013/053250
§ 371 (c)(1),
(2) Date: Oct. 24, 2014

(87) PCT Pub. No.: WO2013/160855
PCT Pub. Date: Oct. 31, 2013

(65) Prior Publication Data
US 2015/0139962 A1  May 21, 2015

(30) Foreign Application Priority Data
Apr. 24, 2012  (PT) .......................................... 106267

(51) Int. Cl.
| | |
|---|---|
| *C12N 5/0789* | (2010.01) |
| *A61K 47/42* | (2017.01) |
| *A61K 47/24* | (2006.01) |
| *A61K 9/06* | (2006.01) |
| *A01N 1/02* | (2006.01) |
| *A61K 35/28* | (2015.01) |

(52) U.S. Cl.
CPC ......... *C12N 5/0647* (2013.01); *A01N 1/0226* (2013.01); *A61K 9/06* (2013.01); *A61K 35/28* (2013.01); *A61K 47/24* (2013.01); *A61K 47/42* (2013.01); *C12N 2500/02* (2013.01); *C12N 2500/36* (2013.01); *C12N 2501/999* (2013.01); *C12N 2533/56* (2013.01)

(58) Field of Classification Search
None
See application file for complete search history.

(56) References Cited

U.S. PATENT DOCUMENTS

| | | | |
|---|---|---|---|
| 2004/0241839 A1 | 12/2004 | Svetlov et al. | |
| 2010/0279412 A1* | 11/2010 | Kato ................... | C12N 5/0031 435/384 |
| 2012/0270780 A1* | 10/2012 | Lee ..................... | C07D 261/02 514/7.7 |

FOREIGN PATENT DOCUMENTS

| | | | |
|---|---|---|---|
| FR | 2 836 828 A1 | 9/2003 | |
| WO | WO 2011/041478 A1 | 4/2011 | |
| WO | WO 2013/103089 A1 | 7/2013 | |

OTHER PUBLICATIONS

Krause et al., CD34: Structure, Biology, and Clinical Utility, Blood, vol. 87, No. 1, Jan. 1, 1996.*
Liu et al., Lysophosphatidic Acid Protects Mesenchymal Stem Cells Against Ischemia-Induced Apoptosis In Vivo, Stem Cells and Development, vol. 18, No. 7, 2009.*
Chen et al., Lysophosphatidic Acid Protects Mesenchymal Stem Cells Against Hypoxia and Serum Deprivation-Induced Apoptosis, Stem Cells 2008; 26:135-145.*
Karliner et al., The Lysophospholipids Sphingosine-1-Phosphate and Lysophosphatidic Acid Enhance Survival during Hypoxia in Neonatal Rat Cardiac Myocytes, J Mol Cell Cardiol 33, 1713-1717 (2001).*
Pedroso, D. C. S. et al. (2011). Improved survival, vascular differentiation and wound healing potential of stem cells co-cultured with endothelial cells. *PLoS One*, 6(1), e16114.
Nakamuta, J. S. et al. (2009). Cell therapy attenuates cardiac dysfunction post myocardial infarction: Effect of timing, routes of injection and a fibrin scaffold. *PLoS One*, 4(6), 1-10.
Chiang, C-L. et al. (2011), Lysophosphatidic acid induces erythropoiesis through activating lysophosphatidic acid receptor 3. *Stem Cells*, 29(11), 1763-1773.
International Search Report, dated Aug. 21, 2013 in connection with PCT International Application No. PCT/IB2013/053250, filed Apr. 24, 2013.
Written Opinion of the International Searching Authority, dated Aug. 21, 2013 in connection with PCT International Application No. PCT/IB2013/053250, filed Apr. 24, 2013.

* cited by examiner

Primary Examiner — Taeyoon Kim
Assistant Examiner — Srikanth Patury
(74) Attorney, Agent, or Firm — John P. White; Cooper & Dunham LLP

(57) ABSTRACT

The present disclosure describes a method and composition for enhancing the survival of hematopoietic stem cells, preferably CD34+ derived from human umbilical cord or peripheral blood, in hypoxic and serum-deprived conditions by cultivating the cells in medium containing lysophosphatidic acid, preferably further comprising a gel, namely a biomimetic gel.
The method and composition may be used in medicine or cosmetic application, in particular, in treatment of cardiac tissue and/or cardiac diseases, and/or in the treatment of wound healing namely diabetic wound healing.

2 Claims, 6 Drawing Sheets

COMPOSITION AND METHOD OF STEM CELLS FOR PRESERVATION OF CARDIAC TISSUE

CROSS-REFERENCE TO RELATED APPLICATIONS

This application is a §371 national stage of PCT International Application No. PCT/IB2013/053250, filed Apr. 24, 2013, claiming priority of Portuguese Patent Application No. 106267, filed Apr. 24, 2012, the contents of each of which are hereby incorporated by reference in their entirety.

TECHNICAL FIELD

The disclosure relates to a composition and method of human hematopoietic stem cells treated with lysophosphatidic acid which enhanced survival in hypoxia and serum deprived conditions and preserves cardiac tissue after myocardial infarction.

BACKGROUND

Heart disease is the leading cause of death and disability in both industrialized nations and the developing world, accounting for approximately 40% of all human mortality. Many patients who survive develop a chronic form of heart disease called congestive heart failure (CHF), which is associated with a progressive deterioration of the heart muscle, scar formation, LV (Left Ventricular) dilation and dysfunction. Patients with severe ischemic heart failure have a high morbidity and mortality, being heart transplant the only available definitive therapy.

Recently, different source of stem cells have been tested in human patients that underwent a MI (Myocardial Infarction), including adult peripheral blood stem cells (APBSCs) and bone marrow-derived stem cells (BMDSCs) (Losordo, D. W., et al., Intramyocardial transplantation of autologous CD34+ stem cells for intractable angina: a phase I/IIa double-blind, randomized controlled trial. Circulation, 2007. 115(25): p. 3165-72; Schachinger, V., et al., Intracoronary bone marrow-derived progenitor cells in acute myocardial infarction. N Engl J Med, 2006. 355(12): p. 1210-21). Improvement in the LV ejection fraction has been reported in the majority of the trials (Schachinger, V., et al., Intracoronary bone marrow-derived progenitor cells in acute myocardial infarction. N Engl J Med, 2006. 355(12): p. 1210-21; Passier, R., L. W. van Laake, and C. L. Mummery, Stem-cell-based therapy and lessons from the heart. Nature, 2008. 453(7193): p. 322-9); however, the functional improvement is still modest (ejection fraction below 5%). Therefore, there is a need for alternative approaches to (i) increase the therapeutic effect of stem cells and to (ii) treat old patients that have adult stem cells with impaired biological activity (e.g. diabetic patients, etc. . . . ) (Passier, R., L. W. van Laake, and C. L. Mummery, Stem-cell-based therapy and lessons from the heart. Nature, 2008. 453(7193): p. 322-9).

CD34+ cells isolated from human cord blood may be a promising cellular therapy for heart regeneration. These stem cells can be used autologously, can differentiate into vascular cells either in vitro or in vivo (Le Ricousse-Roussanne, S., et al., Ex vivo differentiated endothelial and smooth muscle cells from human cord blood progenitors home to the angiogenic tumor vasculature. Cardiovasc Res, 2004. 62(1): p. 176-84) and augment the neovascularization in animal models of myocardial ischemia (Ma, N., et al., Human cord blood cells induce angiogenesis following myocardial infarction in NOD/SCID-mice. Cardiovasc Res, 2005. 66(1): p. 45-54; Hirata, Y., et al., Human umbilical cord blood cells improve cardiac function after myocardial infarction. Biochem Biophys Res Commun, 2005. 327(2): p. 609-14) CD34+ cells isolated from human cord blood have several advantages as compared to APBSCs and BMDSCs, including higher proliferation rate, relatively low risk of giving unwanted cells in vivo (in opposition to the risks described for BMDSCs), and a suitable cell therapy for patients that underwent a MI and have human peripheral blood CD34+ cells with impaired function [5, 10]. For clinical efficacy, it is imperative that stem cells or their progenies survive and engraft into the host tissue. Unfortunately, many cells die a few days after delivery (Ma, N., et al., Human cord blood cells induce angiogenesis following myocardial infarction in NOD/scidSCID-mice. Cardiovasc Res, 2005. 66(1): p. 45-54; Hirata, Y., et al., Human umbilical cord blood cells improve cardiac function after myocardial infarction. Biochem Biophys Res Commun, 2005. 327 (2): p. 609-14; Henning, R. J., et al., Human umbilical cord blood progenitor cells are attracted to infarcted myocardium and significantly reduce myocardial infarction size. Cell Transplant, 2006. 15(7): p. 647-58).

GENERAL DESCRIPTION

An aspect of present disclosure describes a method for enhancing the survival of hematopoietic stem cells, preferably CD34+ derived from human umbilical cord or peripheral blood, in hypoxic and serum-deprived conditions by cultivating the cells in medium containing lysophosphatidic acid, preferably further comprising a gel, namely a biomimetic gel.

This combination surprisingly enhanced survival in hypoxia and serum deprived conditions and preserves cardiac tissue after myocardial infarction. This mixture, especially CD34+ derived from human umbilical cord blood treated with lysophosphatidic acid in fibrin showed improved results.

In an embodiment of the disclosed method, the biomimetic gel may be at least one of the followings: fibrin, hyaluronic acid, alginate, agarose, collagen, PEG derivatives and their mixtures. Preferably fibrin gel, more preferably the fibrin gel comprises a fibrinogen at a final concentration from 1-100 mg/mL and thrombin at a final concentration from 1-500 U/mL. Even more preferably, the fibrin gel comprises a fibrinogen at a final concentration from 10-30 mg/mL and thrombin at a final concentration from 2-50 U/mL.

In an embodiment of the disclosed method the concentration lysophosphatidic varies between 1 and 1000 μM, preferably 100 μM An aspect of present disclosure describes a composition comprising: hematopoietic stem cells, preferably CD34+ derived from human umbilical cord or peripheral blood; with a lysophosphatidic acid, preferably further comprising a gel, namely a biomimetic gel.

This combination surprisingly enhanced survival in hypoxia and serum deprived conditions and preserves cardiac tissue after myocardial infarction. This mixture, especially CD34+ derived from human umbilical cord blood treated with lysophosphatidic acid in fibrin showed improved results.

In an embodiment of the disclosed composition, the biomimetic gel may be at least one of the followings: fibrin, hyaluronic acid, alginate, agarose, collagen, PEG derivatives and their mixtures. Preferably fibrin gel, more preferably the fibrin gel comprises a fibrinogen at a final concentration from 1-100 mg/mL and thrombin at a final concentration from 1-500 U/mL. Even more preferably, the fibrin gel comprises a fibrinogen at a final concentration from 10-30 mg/mL and thrombin at a final concentration from 2-50 U/mL.

An embodiment of the disclosed composition the concentration lysophosphatidic varies between 1 and 1000 µM, preferably 100 µM.

An embodiment of the disclosed composition may comprises $1\times10^{-5}$-$1\times10^{-6}$ of CD34+ cells; and 1-100 µM of lysophosphatidic acid; and 100-200 µL of biomimetic gel.

In other aspect, the disclosed composition may be used in medicine or cosmetic application, namely a pharmaceutical, a medical or a cosmetic composition, namely with CD34+ cells and LPA previous components are in a therapeutically effective amount and may further comprising adequate amounts of excipient. In particular, in treatment of cardiac tissue and/or cardiac diseases, and/or in the treatment of wound healing namely diabetic wound healing.

In an embodiment, the disclosure composition may be an injectable formulation.

In the present disclosure is shown that hematopoietic stem cells, namely CD34+ cells, treated with lysophosphatidic acid (LPA) and cultured under hypoxia and serum deprived conditions double their survival relatively to untreated cells. Surprisingly, the cells proliferate and secrete high levels of cytokines such as IL-4, IL-8 and TNF-α as compared to controls. Finally, LPA-treated cells but not untreated cells preserve cardiac function after myocardial infarction.

DESCRIPTION OF THE FIGURES

The following figures provide preferred embodiments for illustrating the description and should not be seen as limiting the scope of invention.

DETAILED DESCRIPTION

Figure 1:
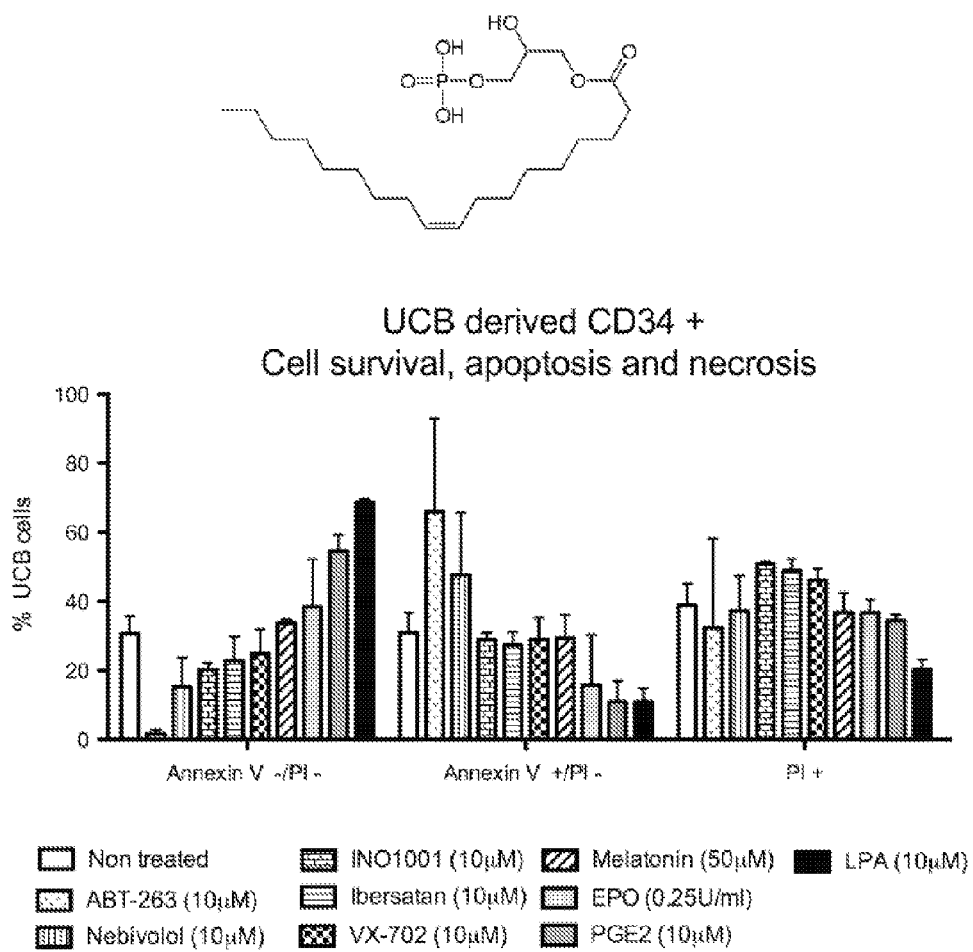
FIG. 1—Chemical structure of LPA. Survival, apoptosis and necrosis of CD34+ cells cultured in hypoxia for 24 h in serum free media with or without drugs. Results are average±SEM (n=2-13).

In the present disclosure is shown that hematopoietic stem cells, namely that CD34+ cells treated with lysophosphatidic acid (LPA) cultured under hypoxia and serum deprived conditions, surprisingly double their survival relatively to untreated cells. Preferably, the cells proliferate and secrete high levels of cytokines such as IL-4, IL-8 and TNF-α as compared to controls. The results show that CD34+ cell survival is mainly mediated by peroxisome proliferator-activator receptor. Finally, the present disclosure shows that LPA-treated cells but not untreated cells preserve cardiac function after myocardial infarction.

The present invention allows the surprising increase of hematopoietic stem cells survival, namely CD34+ cells, (in number and magnitude) the cells proliferation and the therapeutic effect on tissue regeneration and maintain the effect of lysophosphatidic acid.

This effect was unexpectedly observed in hypoxia and serum deprived conditions, and surprisingly was also observed that hematopoietic stem cells, in particular CD34+ cells express LPARs (LPA-receptors) and the effects listed above is achieved by treating to CD34+ with lysophosphatidic acid (LPA).

EMBODIMENTS

Isolation of CD34+ Cells from UCB.

In an embodiment, All human umbilical cord blood (UCB) samples were collected from donors, who signed an informed consent form, in compliance with Portuguese legislation. The collection was approved by the ethical committee of Maternidade Daniel de Matos. The samples were stored in sterile bags containing 35 mL of citrate-phosphate-dextrose anticoagulant solution. CD34+ cells were isolated from mononuclear cells, obtained from UCB samples after Ficoll (preferably, Histopaque-1077 Hybri Max; preferably, Sigma-Aldrich, St. Louis, USA) density gradient separation. CD34+ cells were positively selected (2 times) using the mini-MACS immunomagnetic separation system (preferably, Miltenyi Biotec, Bergisch Gladbach, Germany, http://www.miltenyibiotec.com), according to the manufacturer's recommendations. CD34+ cells were immediately used for cell encapsulation studies or in vivo experiments without further treatment. The cells isolated were above 95% pure for CD34 antigen as confirmed by FACS. These cells are CD34+CD45+CD31+KDR−vWF−CD14− (Pedroso, D. C., et al., Improved survival, vascular differentiation and wound healing potential of stem cells co-cultured with endothelial cells. PLoS One, 2011. 6(1): p. e16114).

Cell Treatment.

In an embodiment, UCB CD34+ cells ($1\times10^6$ cells/mL) were incubated in X-Vivo media (Lonza) in a hypoxia chamber for 24 h (0.5% of $O_2$ and 5% of $CO_2$), in the presence or absence of pharmacological drugs, for further assessment of cell survival/apoptosis and necrosis by FACS analysis of the expression of annexin V and PI respectively. Preferably, cells were pretreated with the respective drugs for 1 hour before hypoxia, and treatment maintained during hypoxia.

Immunostaining.

In an embodiment, cells were fixed with 4% (v/v) paraformaldehyde (preferably, EMS, Hatfield, USA) for 15-20 minutes at room temperature. After blocking for 30 minutes with 1% (w/v) bovine serum albumin (BSA) solution (preferably, Sigma-Aldrich), the cells were stained for 1 h with anti-human monoclonal antibodies PPARγ and CD34. In each immunofluorescence experiment, an isotype-matched IgG control was used. The binding of primary antibodies to specific cells was detected with anti-mouse IgG Cy3 conjugate (preferably, Sigma-Aldrich). The nucleus of cells was stained with 4',6-diamidino-2-phenylindole (preferably, DAPI; Sigma-Aldrich). After the indirect labelling, the cells were examined preferably, with a Zeiss fluorescence microscope.

Flow cytometry.

In an embodiment, multicolor analysis for progenitor and stem cell phenotyping was performed on a FACS Calibur cytometer (preferably, Becton Dickinson). Cells were stained for 1 h with APC or pacific blue antihuman CD45 (preferably, e-Bioscience), FITC anti-mouse CD45 (preferably, -Bioscience), PeCy7 anti-human CD33 (preferably, BD Bioscience), PE anti-human CD11b (preferably, BD Bioscience), FITC anti-human CD19 (preferably, BD Bioscience), PeCy7 anti-human CD3 (preferably, BD Bioscience), PE anti-human Glycophorin A (preferably, BD Bioscience), FITC anti-human CD41 (preferably, e-bioscience), and PeCy7 anti-human CD56 (preferably, BD Bioscience), washed with staining media and analyzed.

Preparation of Fibrin Gels.

In an embodiment, fibrin gels were formed by crosslinking of fibrinogen in the presence of thrombin (both from Sigma-Aldrich). The fibrinogen solution was prepared by dissolving human fibrinogen in Tris-buffered saline (TBS) (preferably, Sigma-Aldrich), pH 7.4 (20 mg/mL), and then sterilized by filtering through a 0.22 μm syringe filter (Acrodisc, Pall, NY, USA). Fresh thrombin solutions were prepared by dissolving human thrombin in TBS at pH 7.4 at a concentration of 50 U/mL. Fibrin gels (200 μL, unless otherwise stated) were prepared by mixing three different components: fibrinogen (10 mg/mL), $CaCl_2$ (preferably, Merck, NJ, USA) (2.5 μM) and thrombin (0.2 U/mL). This solution was allowed to gel at 37° C. and 100% relative humidity.

Degradation of Fibrin Gels.

In an embodiment, gel precursor solution was prepared by mixing Alexa Fluor® 488 human fibrinogen conjugate (preferably, Invitrogen) (0.156 mg) to unlabeled fibrinogen (9.844 mg) in 1 mL of TBS. The degradation rate of fibrin gels with or without cells over time was indirectly estimated by the decrease of their fluorescence. Their fluorescence was measured immediately at time zero and at the desired time points. Complete degradation of the gels was induced by incubation with 200 μL of a solution of human plasmin (preferably, Sigma-Aldrich) in TBS (0.006 U per gel) for an overnight at 37° C. Following centrifugation, the fluorescence of the supernatant fractions was measured at 520 nm in a SPECTRAmax Gemini EM fluorescence microplate reader (preferably, Molecular Devices, Sunnyvale, Calif., USA, www.moleculardevices.com).

Cytokine Secretion Analyses.

In an embodiment, cell culture supernatants were evaluated for the presence and concentrations of cytokines using a Bio-Plex Pro Human Cytokine 17-Plex Panel Assay (preferably, Bio-Rad, Hercules, Calif., USA), according to manufacturer's instructions, in a Bio-Plex 200 System (Bio-Rad, www.bio-rad.com). The human Group I 17-Plex Panel consisted of the following analytes: interleukin-1β (IL-1β), IL-2, IL-4, IL-5, IL-6, IL-7, IL-8; IL-10, IL-12(p70), IL-13, IL-17, granulocyte colony-stimulating factor (G-CSF), granulocyte/macrophage colony-stimulating factor (GM-CSF), interferon-γ (IFN-γ), monocyte chemotactic protein (monocyte chemotactic activating factor [MCP-1 (MCAF)], macrophage inflammatory protein-β (MIP-1 β) and tumor necrosis factor-α (TNF-α). Supernatant media samples were collected, centrifuged to remove precipitates and frozen. A standard range of 0.2 to 3,200 pg/mL was used. Samples and controls were run in triplicate, standards and blanks in duplicate.

Quantitative Reverse Transcription-Polymerase Chain Reaction (qRT-PCR) Analysis.

In an embodiment, total RNA in cells was extracted by using the RNeasy Mini Kit (preferably, Qiagen, Valencia, USA), according to manufacturer's instructions. Cells were initially centrifuged and homogenized in Trizol. In all cases, cDNA was prepared from 1 pg total RNA using Taqman Reverse transcription reagents (preferably, Applied Biosystems, Foster City, USA). Quantitative PCR (qPCR) was performed using Power SYBR Green PCR Master Mix (preferably, Applied Biosystems) and the detection was carried out in a 7500 Fast Real-Time PCR System (preferably, Applied Biosystems, www.appliedbiosystems.com). Quantification of target genes was performed relatively to the reference (human or mouse, depending on the type of cells under analysis) GAPDH gene: relative expression=2 [−(Ctsample−CtGADPH)]. The mean minimal cycle threshold values (Ct) were calculated from four independent reactions. Primer sequences are published as supporting information (Table S1).

Myocardial Infarction Animal Model.

In an embodiment, nude rats were anaesthetized with ketamine (75 mg/kg, IP) and dexmedetomidine (0.375 mg/kg, IP). Anaesthesia with 2-3% isoflurane in balanced oxygen was provided. The abdomen and anterior chest were scrubbed with betadine and wiped with 70% alcohol (with several cycles of betadine scrub followed by alcohol rinse and application of betadine solution). The heart was approached either by a transverse abdominal incision (diaphragmatic incision) with the animal's back gently extended over a soft towel or laterally via the intercostal space 4-5. Instruments were sterilized by Autoclave. A small diaphragmatic incision was made to create a pericardial window. A 5 mm incision was made in the pericardium with an 11-0 scalpel. Myocardial infarction was induced by permanently ligation of the left anterior descending coronary artery with a 6-0 Proline suture, 2-3 mm below the origin of the artery. Pallor and regional wall motion abnormality of the left ventricle confirmed occlusion. The pericardium was left open or removed to avoid tamponade. The pleural space was evacuated with an 18-gauge sterile needle and 3-mL syringe following closure of the pleural cavity. Abdominal wall and subcutaneous tissue was closed with Vicryl 4-0 followed by a subcuticular closure with Vicryl 4-0. The animal was extubated and then allowed to recover. Each animal was maintained during surgical procedures and recovery under warming pads until awake and able to ambulate. Two days after recovery from this procedure, animals underwent echocardiographic evaluation under ketamine/midazolam anesthesia. Animals meeting the echocardiographic inclusion criterion (fractional shortening below 50%) were stratified into one of 4 groups. The rats were then subjected to a second thoracotomy followed by direct injection of 100 µL of therapeutic agent using a Hamilton syringe (preferably Hamilton Company) and a 30-gauge needle. In the following day, the animals were monitored by echocardiography. Two weeks after implantation, the surviving rats were again analyzed by echocardiography. At week 3, animals were sacrificed by euthanasia. The heart and various organs were harvested, fixed in methyl Carnoy's solution and processed for histological analysis.

LPA Induces CD34+ Cell Survival in Hypoxia and Serum Deprived Conditions

Figure 2:
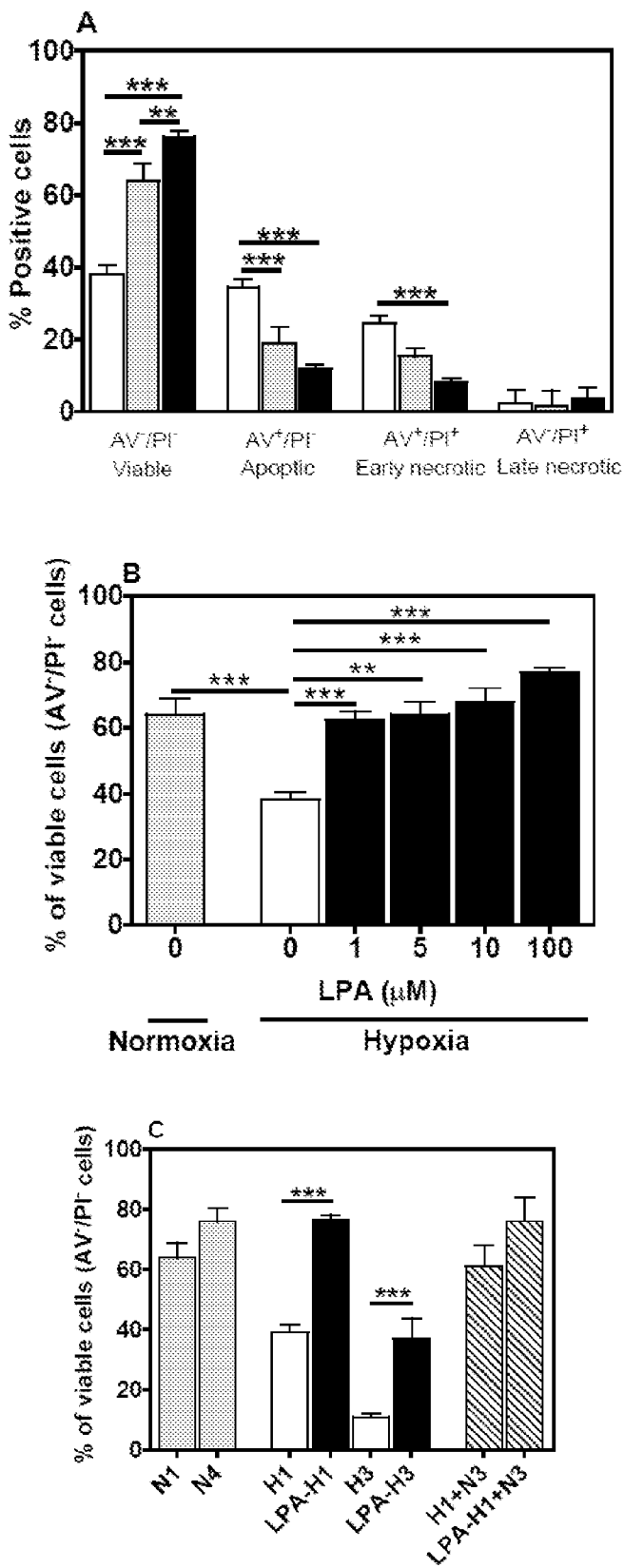
FIG. 2—LPA improves CD34+ cell survival in cells cultured in hypoxia and serum deprived conditions. (A) Survival, apoptosis and necrosis of CD34+ cells cultured in serum free media for 24 h in normoxia, hypoxia and hypoxia with LPA treatment. (B) Effect of LPA concentration in the survival of CD34+ cells cultured in serum free media for 24 h in hypoxia or normoxia. (C) Effect of LPA in the survival of cells cultured in hypoxia for 1 (H1) or 3 days (H3), in hypoxia for 1 day and 3 days in normoxia (H1+N3), or normoxia for 1 (Ni) or 4 days (N4). In all graphs, cells were cultured with or without LPA (100 µM). Results are average±SEM (n=4-50). In all figures, * denote statistical significance: *P<0.05, *P<0.01, **P<0.001.

In a preferred embodiment, to identify molecules that promote CD34+ cell survival in hypoxia and serum deprived conditions we developed an assay that uses human umbilical cord blood derived CD34+ cells ($2 \times 10^{-5}$ cells per well of a 96-well plate) suspended in X-Vivo medium (used in clinical trials (Schachinger, V., et al., Intracoronary bone marrow-derived progenitor cells in acute myocardial infarction. N Engl J Med, 2006. 355(12): p. 1210-21)) and incubated in a hypoxia chamber at 0.5% $O_2$, at 37° C., for 24 h. Some of the drugs selected have been approved by FDA for the treatment of cardiovascular diseases (e.g. Nebivolol Lombardo, R. M., et al., Effects of nebivolol versus carvedilol on left ventricular function in patients with chronic heart failure and reduced left ventricular systolic function. Am J Cardiovasc Drugs, 2006. 6(4): p. 259-63; Ibersatan Massie, B. M., et al., Irbesartan in patients with heart failure and preserved ejection fraction. N Engl J Med, 2008. 359(23): p. 2456-67), others are being evaluated in pre-clinical/clinical assays to improve heart function in patients/models with heart failure (e.g. INO1001 (Szabo, G., et al., INO-1001 a novel poly (ADP-ribose) polymerase (PARP) inhibitor improves cardiac and pulmonary function after crystalloid cardioplegia and extracorporal circulation. Shock, 2004. 21(5): p. 426-32); erythropoietin (Belonje, A. M., et al., Effects of erythropoietin after an acute myocardial infarction: rationale and study design of a prospective, randomized, clinical trial (HEBE III). Am Heart J, 2008. 155(5): p. 817-22); melatonin (Chen, Z., et al., Protective effect of melatonin on myocardial infarction. Am J Physiol Heart Circ Physiol, 2003. 284(5): p. H1618-24); VX-702 (Ma, X. L., et al., Inhibition of p38 mitogen-activated protein kinase decreases cardiomyocyte apoptosis and improves cardiac function after myocardial ischemia and reperfusion. Circulation, 1999. 99(13): p. 1685-91)), others are natural substances found in the human body (LPA). Cell viability was evaluated by flow cytometry using Annexin V/propidium iodide (PI) staining. Annexin V is a phospholipid-binding protein with specificity for phospatidyl serine, one of the earliest makers of cellular transition to an apoptotic state. This phospholipid is translocated from the inner to the outer leaflet of the plasma membrane (Koopman, G., et al., Annexin V for flow cytometric detection of phosphatidylserine expression on B cells undergoing apoptosis. Blood, 1994. 84(5): p. 1415-20.). PI enters in necrotic cells and binds to double-stranded nucleic acids, but is excluded from cells with normal integrity [20]. According to FIG. 1, untreated CD34+ cells show a very poor survival, with only ~31% of viable cells, ~31% of apoptotic cells (Annexin V+/PI−) being the majority of the cells ~39% at the necrotic stage (PI+). Of ten drugs tested, LPA, prostaglandin E2 (PGE2) and erythropoietin improved significantly (P<0.001) cell survival. LPA (10 µM) was the drug with the highest pro-survival effect (~69% of viable cells) and therefore further studied (FIGS. 1 and 2A). Surprisingly LPA improves cell survival by reverting necrosis and apoptosis of CD34+ cells especially under hypoxic and serum deprived conditions.

The pro-survival effect of LPA was concentration dependent (from 1-100 µM) being the survival of CD34+ cells already statistically significant (P<0.001, n=6) as compared to the control (untreated cells) at 1 µM of LPA (FIG. 2B). Importantly, the percentage of viable cells in CD34+ treated with 1 µM of LPA and cultured under hypoxia conditions is similar to untreated cells cultured under normoxia conditions. The pro-survival effect of LPA decreases as a function of hypoxia time (FIG. 2C). The percentage of viable cells in LPA-treated CD34+ cells decreased from 78% at day 1 to 40% at day 3. All together, the results obtained surprisingly indicate that LPA is a pro-survival molecule of CD34+ cells and its effect is time- and concentration-dependent.

Figure 3:
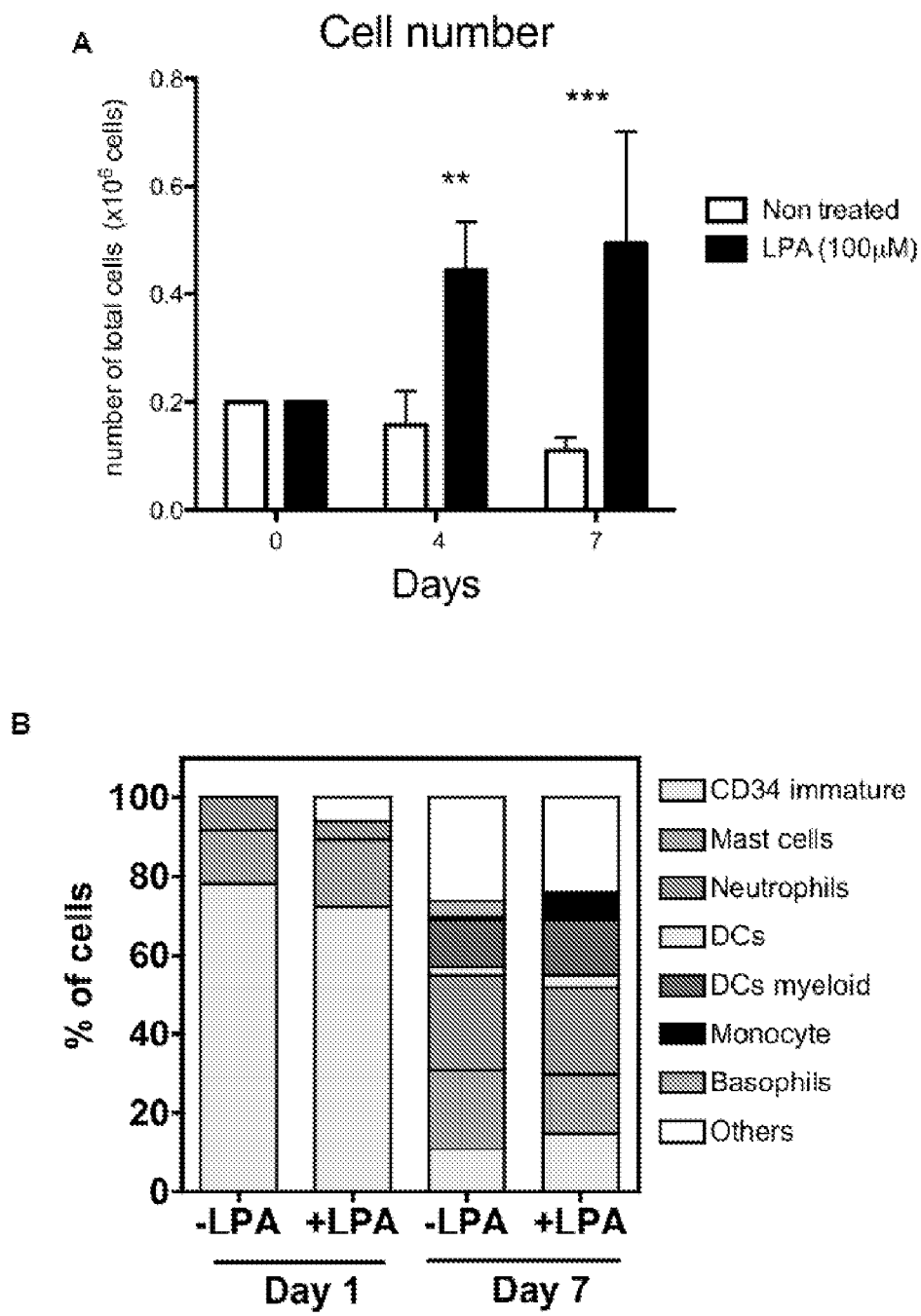
FIG. 3—LPA affects cell proliferation and has minimal impact in cell differentiation in hypoxia and serum deprived conditions. (A) Number of total cells after 1 day in hypoxia and 3 or 6 days in normoxia. (B) Cell differentiation as measured by flow cytometry (n=1). Cells were cultured in hypoxia for 1 day followed or not by 6 days in normoxia. In all graphs, cells were cultured with or without LPA (100 µM).

LPA Induces Cell Proliferation without the Expansion of Early Multipotent Progenitor Cells LPA is highly mitogenic for quiescent cells [21]. The mitogenic action of LPA involves the activation of a pertussis toxin-insensitive G protein with subsequent $Ca^{2+}$ mobilization and stimulation of protein kinase C, release of arachidonic acid in a GTP-dependent manner, and activation of a pertussis toxinsensitive Gi protein mediating inhibition of adenylate cyclase (van Corven, E. J., et al., Lysophosphatidate-induced cell proliferation: identification and dissection of signaling pathways mediated by G proteins. Cell, 1989. 59(1): p. 45-54). To determine whether LPA can induce the proliferation of CD34+ cells, a suspension of untreated or LPA-treated cells ($2 \times 10^{-5}$ cells in 200 µL of X-vivo medium) was exposed to hypoxia for 24 h and then cultured under normoxia conditions for 6 additional days. LPA-treated cells increased their number approximately 3-fold over the 7 days period while untreated cells decreased to half of their initial number (FIG. 3A).

To examine the effect of LPA in CD34+ cell self-renewal/differentiation, untreated and LPA-treated CD34+ cells were cultured in X-vivo medium in hypoxia conditions for 1 day followed or not by 6 days in normoxia and finally characterized by FACS. After 1 day of hypoxia, both untreated or LPA-treated CD34+ cells started to differentiate into mast cells (between 14 and 17%) and neutrophils (between 5 and 8%) (FIG. 3B). Only 78% and 72% of the untreated or LPA-treated CD34+ cells express CD34 marker. CD34 expression is higher in cells that have been exposed to hypoxia than in normoxia conditions since only 6% of the cells cultured in normoxia conditions for 24 h express CD34 marker. Cells cultured for 1 day in hypoxia and then 6 days in normoxia further differentiate into several cell lineages including dendritic cells (DCs), basophils, monocytes, neutrophils and mast cells. Similar differentiation profiles were observed for untreated and LPA-treated cells.

Figure 4:
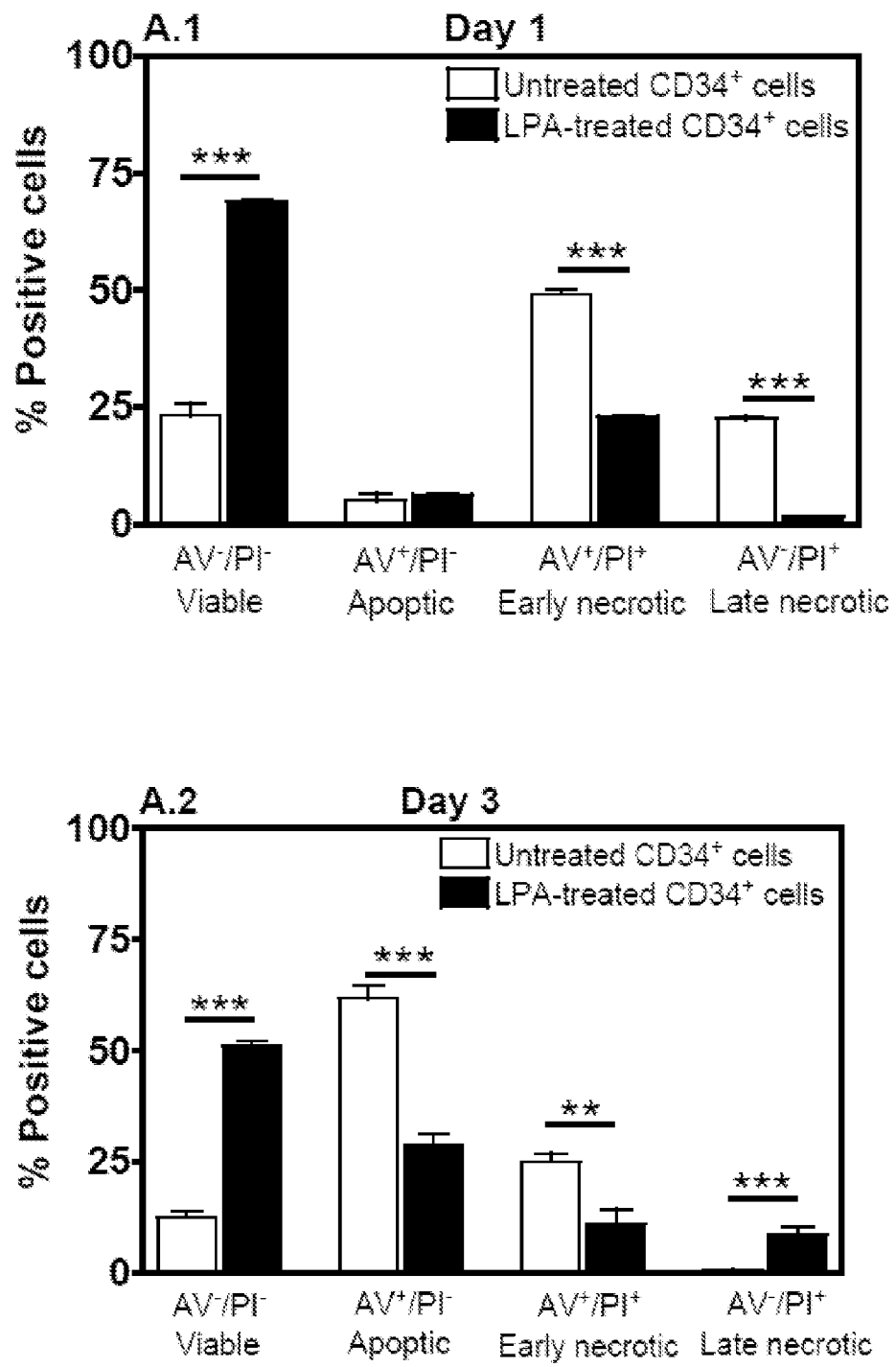
FIG. 4—LPA affects cell survival in CD34+ cells encapsulated in fibrin gel and cultured in hypoxia and serum deprived conditions. (A.1) Cells were cultured in serum free media with or without LPA (100 µM) and in hypoxia for 1 day. (A.2) Cells were cultured in serum free media with or without LPA (100 µM) and in hypoxia for 3 days. In all graphs, results are average±SEM (n=3-6). In all figures, * denote statistical significance: *P<0.05, P<0.01, P<0.001.

LPA Induces CD34+ Cell Survival in Cells Encapsulated in Fibrin Gels and Cultured in Hypoxia and Serum Deprived Conditions Injectable scaffolds are very promising vehicles to deliver stem cells for regenerative medicine since they provide a favorable structural support for cell survival and proliferation (Pedroso, D. C., et al., Improved survival, vascular differentiation and wound healing potential of stem cells co-cultured with endothelial cells. PLoS One, 2011. 6(1): p. e16114; Kraehenbuehl, T. P., R. Langer, and L. S. Ferreira, Three-dimensional biomaterials for the study of human pluripotent stem cells. Nat Methods, 2011. 8(9): p. 731-6; Nakamuta, J. S., et al., Cell therapy attenuates cardiac dysfunction post myocardial infarction: effect of timing, routes of injection and a fibrin scaffold. PLoS One, 2009. 4(6): p. e6005.). Several studies have shown that cells transplanted with scaffolds in the cardiac setting improved cell survival, induced angiogenesis and preserved cardiac function after infarction (Nakamuta, J. S., et al., Cell therapy attenuates cardiac dysfunction post myocardial infarction: effect of timing, routes of injection and a fibrin scaffold. PLoS One, 2009. 4(6): p. e6005; Christman, K. L., et al., Fibrin glue alone and skeletal myoblasts in a fibrin scaffold preserve cardiac function after myocardial infarction. Tissue Eng, 2004. 10(3-4): p. 403-9; Kraehenbuehl, T. P., et al., Human embryonic stem cell-derived microvascular grafts for cardiac tissue preservation after myocardial infarction. Biomaterials, 2011. 32(4): p. 1102-9; Kutschka, I., et al., Collagen matrices enhance survival of transplanted cardiomyoblasts and contribute to functional improvement of ischemic rat hearts. Circulation, 2006. 114(1 Suppl): p. I167-73). Recently, we demonstrated that CD34+ cells have greater initial adhesion to fibrin gels than to polystyrene dishes, collagen and fibronectin (Pedroso, D. C., et al., Improved survival, vascular differentiation and wound healing potential of stem cells co-cultured with endothelial cells. PLoS One, 2011. 6(1): p. e16114). Furthermore, is shown that fibrin gels support the survival of CD34+ cells for at least 10 days and the gels resist to the degradation of metalloprotease enzymes (Pedroso, D. C., et al., Improved survival, vascular differentiation and wound healing potential of stem cells co-cultured with endothelial cells. PLoS One, 2011. 6(1): p. e16114). In a preferred embodiment, to examine whether fibrin gels support CD34+ cell survival in hypoxia and serum deprived conditions were encapsulated untreated or LPA-treated cells ($2\times10^{-5}$) in fibrin gel (200 µL) and incubated in a hypoxia chamber at 0.5% $O_2$, at 37° C., for 1 and 3 days. Cell viability was evaluated by flow cytometry using Annexin V/propidium iodide (PI) staining. Untreated CD34+ cells have poor survival in fibrin gels (23.2±2.8% of viable cells, n=3, at day 1; 12.6±1.2% of viable cells, n=5, at day 3) showing that the matrix alone does not have any pro-survival effect (FIG. 4). In contrast, LPA-treated CD34+ cells encapsulated in fibrin gels present high survival, comparable to values observed in LPA-treated cells not encapsulated in fibrin gels (day 1: 69.0±0.7% vs 76.7±1.5% for encapsulated and non-encapsulated, respectively; day 3: 51.1±0.8% vs 37.2±6.6% for encapsulated and non-encapsulated, respectively).

LPA Induces CD34+ Cell Survival Mainly Through Peroxisome Proliferator-Activator Receptor (PPAR)

Figure 5:
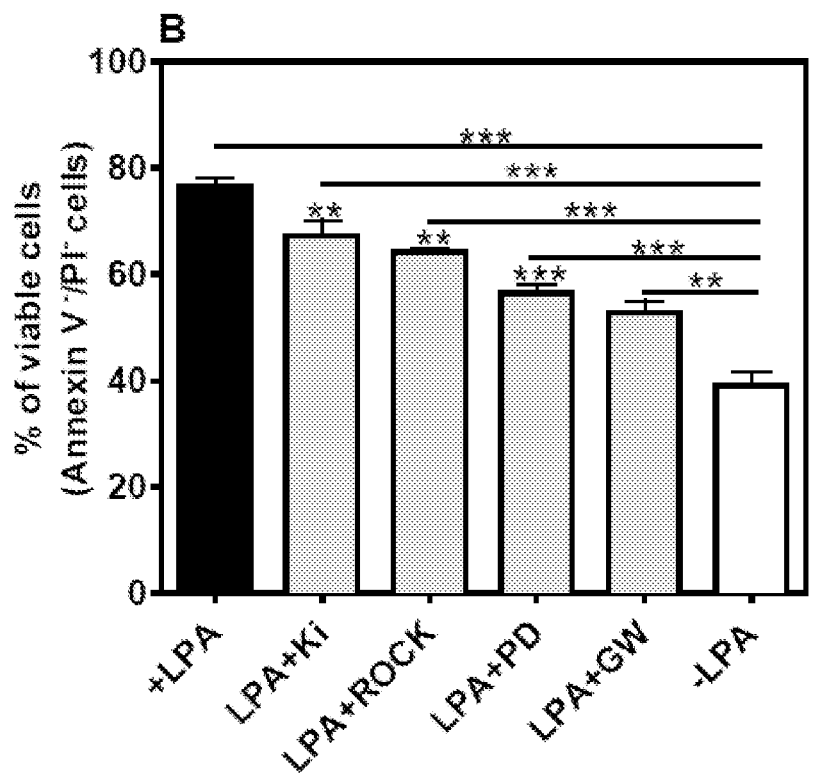
FIG. 5—LPA induces CD34+ cell survival mainly through peroxisome proliferator-activator receptor (PPAR). Cells were cultured in serum free medium with LPA. Cells were pretreated with Rho kinase inhibitor (Y-2762, 50 µM), mitogen-activated protein kinase (MAPK) inhibitor (PD98059, 60 µM), LPA1- and LPA3-specific inhibitor (Ki16425, 10 µM), or peroxisome proliferator-activator receptor g (PPARg) inhibitor (GW9662, 50 µM) for 1 hour before hypoxia and cell medium containing LPA (100 µM) for 24 h. Cells without any pretreatment and cultured in serum free medium with or without LPA, in hypoxia for 24 h, were used as positive and negative controls, respectively. Results are average±SEM (n=3-6). * Denote statistical significance: *P<0.05, P<0.01, P<0.001.

The biological roles of LPA are diverse and include developmental, physiological, and pathophysiological effects (Lin, M. E., D. R. Herr, and J. Chun, Lysophosphatidic acid (LPA) receptors: signaling properties and disease relevance. Prostaglandins Other Lipid Mediat, 2010. 91(3-4): p. 130-8). To date up to five LPA receptors (LPARs) have been identified: LPA1-LPA5 (Choi, J. W., et al., LPA receptors: subtypes and biological actions. Annu Rev Pharmacol Toxicol, 2010. 50: p. 157-86). The receptors are G protein-coupled receptors (GPCRs) and their presence can be found in multiple tissues. LPA1, LPA2 and LPA3 are widely expressed in most tissues (Ishii, I., et al., Functional comparisons of the lysophosphatidic acid receptors, LP(A1)/VZG-1/EDG-2, LP(A2)/EDG-4, and LP(A3)/EDG-7 in neuronal cell lines using a retrovirus expression system. Mol Pharmacol, 2000. 58(5): p. 895-902). LP4 is expressed in specific organs, such as the pancreas, ovaries and thymus (Lee, C. W., et al., LPA(4)/GPR23 is a lysophosphatidic acid (LPA) receptor utilizing G(s)-, G(q)/G(i)-mediated calcium signaling and G(12/13)-mediated Rho activation. J Biol Chem, 2007. 282(7): p. 4310-7). LPA5 is expressed at low levels in multiple tissues (Lee, C. W., et al., GPR92 as a new G12/13- and Gq-coupled lysophosphatidic acid receptor that increases cAMP, LPA5. J Biol Chem, 2006. 281(33): p. 23589-97). To identify the receptor that is mediating the pro-survival effect of LPA (100 µM), was used Ki16425 (10 µM), an LPA1- and LPA3-specific antagonist, and GW9662 (50 µM), an antagonist of peroxisome proliferator-activator receptor γ (PPAR γ). Studies indicate that LPA has a high affinity by this last receptor (McIntyre, T. M., et al., Identification of an intracellular receptor for lysophosphatidic acid (LPA): LPA is a transcellular PPARgamma agonist. Proc Natl Acad Sci USA, 2003. 100(1): p. 131-6; Gustin, C., M. Van Steenbrugge, and M. Raes, LPA modulates monocyte migration directly and via LPA-stimulated endothelial cells. Am J Physiol Cell Physiol, 2008. 295(4): p. C905-14). This approach was complemented, by inhibiting downstream targets of the receptors including Rho kinase and mitogen-activated protein kinase (MAPK) using Y-2762 (50 µM) and PD98059 (60 µM) antagonists, respectively. It is known that all LPARs couple with and activate G proteins, which in turn activate MAPK (LPA1, LPA2, LPA3 and LPA4) and Rho kinase (LPA1, LPA2, LPA4 and LPA5) (Choi, J. W., et al., LPA receptors: subtypes and biological actions. Annu Rev Pharmacol Toxicol, 2010. 50: p. 157-86). Cells were treated for 1 h in X-Vivo medium containing a specific antagonist followed by culture under hypoxia conditions for 24 h. Cell survival was assessed by FACS analysis after Annexin V/PI staining. Results indicate that under the conditions tested PPARγ mainly mediates the pro-survival effect of LPA (FIG. 5B). The antagonist of PPARγ significantly decreased (P<0.001, n=11) the number of viable cells induced by LPA from ~77% to ~53%; however, it did not block totally the pro-survival effect of LPA, since cells without LPA have a survival of 39% (P<0.01). The inhibition of LPA1 and LPA3 by Ki16425 had a relatively small effect in the survival of CD34+ cells (FIG. 5B). The number of viable cells decreased from 77% (+LPA) to 67% (P<0.01, n=19). Importantly, the inhibition of MAPK signaling pathway suppressed at higher levels the pro-survival effect of LPA than the inhibition of Rho kinase signaling pathway. Because the two signaling pathways are downstream targets of different LPARs (see above), this might indicate different contributions of LPARs in the survival of CD34+ cells. Taken together, data show that LPA is able to promote CD34+ cell survival in hypoxic and serum-deprived conditions mainly through the activation of PPARγ.

LPA Modulates CD34+ Cell Cytokine Release

To determine the effect of LPA in the release of signaling cytokines and growth factors by CD34+ cells, was used a cytokine bead array. The cells were incubated in serum free medium X-Vivo for 24 h under normoxia or hypoxia conditions, either in the presence or absence of LPA (100 μM). Untreated CD34+ cells in normoxia express high levels (>100 pg/mL) of IL-8 and MIP-1b, medium levels (between 100 and 1 pg/mL) of IL-6, TNF-α and GM-CSF, and low levels (<1 pg/mL) of IL-1β, IL-4 and IL-17 (FIG. 5C). CD34+ cells cultured in hypoxia and serum deprived conditions express significantly higher levels of IL-1β (~8 fold), IL-4 (~2 fold), IL-6 (~1.2 fold), IL-8 (~10 fold), IL-17 (~4 fold) and GM-CSF (~2 fold), than in normoxia conditions. Interestingly, CD34+ cells cultured in hypoxia and serum deprived conditions but in the presence of LPA increase the secretion of IL-4 (from ~0.9 to ~2.7 pg/mL), IL-8 (from ~10,000 to ~17,000 pg/mL) and TNF-α from ~3 to ~15 pg/mL) and decrease the secretion of IL-1 (from ~9 to ~2 pg/mL), IL-6 (from ~4 to ~2 pg/mL) and GM-CSF (from ~4 to ~1 pg/mL) as compared to cells cultured under the same conditions but in the absence of LPA.

LPA-Treated CD34+ Cells Preserve Cardiac Function after Myocardial Infarction

Figure 6:
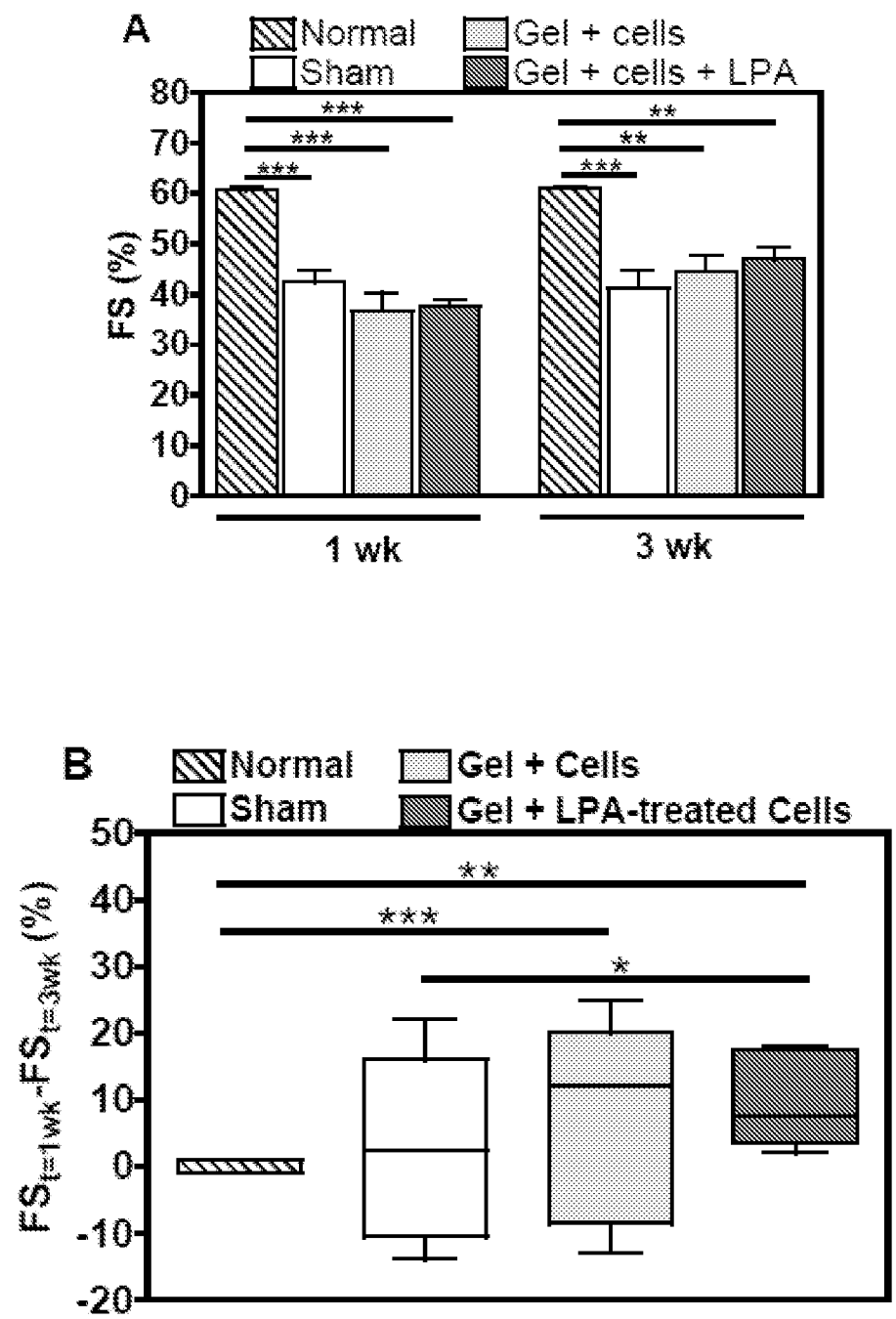
FIG. 6—LPA-treated CD34+ cells preserve cardiac function after myocardial infarction. Myocardial infarctions were induced by permanent ligation of the left anterior descending coronary artery (LAD). (A) Cardiac fractional shortening in animals with (sham, gel+CD34+ cells, gel+LPA-treated CD34+ cells) or without ligation of LAD (normal). In LPA-treated CD34 cells, the cells were treated with 100 µM of LPA, 1 h before transplantation. Cells ($1\times10^{-6}$ cells) were delivered in a fibrin gel precursor solution (100 mL) into the infarcted heart of nude rats. (B) Cardiac fractional shortening at week 3 normalized by week 1. In all graphs, results are average±SEM (n=6-10). * Denote statistical significance: *P<0.05, P<0.01, P<0.001

It has been shown that the transplantation of human CD34+ cells in heart after infarction improves left ventricle ejection fraction and preserves heart tissue. To evaluate the therapeutic potential of LPA-treated CD34+ cells the cells were delivered ($1 \times 10^{-6}$ cells) treated with LPA (100 μM) in a fibrin gel precursor solution (100 μL) into the infarcted heart of nude rats. Myocardial infarctions were induced by permanent ligation of the left anterior descending coronary artery (LAD). Infarcted hearts without any treatment (sham) or treated with CD34+ cells suspended in a fibrin gel precursor solution were used as controls. After 2 weeks post-implantation, the functional properties of the heart were evaluated by echocardiography. Left ventricles of control rat had a mean fractional shortening of 42.7±1.6 (n=10) and 41.6±3.8 (n=10) at time 1 day and 2 weeks, respectively; rats treated with CD34+ cells encapsulated in a fibrin gel precursor solution had a mean fractional shortening of 36.7±3.4 (n=6) and 44.5±3.0 (n=6) at time 1 day and 2 weeks, respectively; and finally rats treated with LPA-treated CD34+ cells and encapsulated in a fibrin gel precursor solution had a mean fraction shortening of 37.5±1.2 (n=6) and 47.0±2.0 (n=6) at time 1 day and 2 weeks, respectively (FIG. 6A). Because the initial fractional shortening is different between experimental groups were used the difference of the fractional shortenings at 2 weeks and day 1 to compare the therapeutic effectiveness of the treatments (FIG. 6B). The median of the differences in the fractional shortenings was 7.5 and 2.6 in LPA-treated cells+gel and sham groups, respectively, being the differences statistically significant (P<0.05). No statistical differences were observed between hearts treated with CD34+ cells and sham (P>0.05). Taken together, the delivery of LPA-treated CD34+ cells into the infarcted heart improve cardiac fractional shortening, and the effect was superior to untreated CD34+ cells.

The invention is of course not in any way restricted to the embodiments described and a person with ordinary skill in the art will foresee many possibilities to modifications thereof without departing from the basic idea of the invention as defined in the appended claims.

The following claims set out particular embodiments of the invention.

The invention claimed is:

1. A method for enhancing the survival of hematopoietic stem cells in hypoxic and serum-deprived conditions, the method comprising cultivating the hematopoietic stem cells in a medium containing lysophosphatidic acid, wherein the concentration of lysophosphatidic acid is 100 μM, so as to enhance the survival of the hematopoietic stem cells in hypoxic and serum-deprived conditions.

2. The method according to claim 1 wherein the hematopoietic stem cells are CD34+ cells.

* * * * *

UNITED STATES PATENT AND TRADEMARK OFFICE
CERTIFICATE OF CORRECTION

PATENT NO. : 9,868,935 B2
APPLICATION NO. : 14/397122
DATED : January 16, 2018
INVENTOR(S) : Lino Da Silva Ferreira and Isabel Maria Fidalgo Dos Santos Silva Carvalho Page 1 of 1

It is certified that error appears in the above-identified patent and that said Letters Patent is hereby corrected as shown below:

On the Title Page

Item (73) incorrectly indicates the assignee to be:
-- (73) Assignee: CRIOESTAMINAL, SAÚDE E TECNOLOGIA, SA., Cantanhede (PT) --
Please correct to indicate:
-- (73) Assignee: STEMLAB, S.A., Cantanhede (PT) --.

Signed and Sealed this
Eighteenth Day of September, 2018

Andrei Iancu
*Director of the United States Patent and Trademark Office*